(12) United States Patent
Seyr et al.

(10) Patent No.: US 9,546,976 B2
(45) Date of Patent: Jan. 17, 2017

(54) METHOD AND APPARATUS FOR MEASUREMENT OF THE OXYGEN CONTENT OR THE OXYGEN PARTIAL PRESSURE IN A MEASUREMENT GAS

(71) Applicant: Sensore Electronic GmbH, Klosterneuburg (AT)

(72) Inventors: Peter Seyr, Vienna (AT); Werner Reiter, Klosterneuburg (AT)

(73) Assignees: Werner Reiter, Klosterneuburg (AT); Peter Klaus Soukop, Gramatneusiedl (AT)

( * ) Notice: Subject to any disclaimer, the term of this patent is extended or adjusted under 35 U.S.C. 154(b) by 747 days.

(21) Appl. No.: 13/855,257

(22) Filed: Apr. 2, 2013

(65) Prior Publication Data

US 2013/0264223 A1    Oct. 10, 2013

(30) Foreign Application Priority Data

Apr. 5, 2012 (DE) .................. 10 2012 103 005
Mar. 25, 2013 (DE) .................. 10 2013 103 003

(51) Int. Cl.
*G01N 27/409* (2006.01)
*G01N 27/406* (2006.01)
*G01N 27/419* (2006.01)

(52) U.S. Cl.
CPC ........ *G01N 27/409* (2013.01); *G01N 27/4065* (2013.01); *G01N 27/419* (2013.01)

(58) Field of Classification Search
CPC ..... G05D 23/24; G01M 15/10; G01M 15/102; G01M 15/104; G01N 27/404–27/407; G01N 27/409; G01N 27/419; G01N 27/41
See application file for complete search history.

(56) References Cited

U.S. PATENT DOCUMENTS

| 4,900,425 | A | | 2/1990 | Sasayama et al. |
| 6,093,294 | A | * | 7/2000 | Kato ............ G01N 27/407 204/425 |
| 6,200,458 | B1 | | 3/2001 | Brida et al. |
| 6,303,012 | B1 | * | 10/2001 | Inoue ............ G01N 27/417 204/425 |
| 2008/0206108 | A1 | * | 8/2008 | Anilkumar ...... G01N 27/4065 422/94 |

FOREIGN PATENT DOCUMENTS

DE    19800027    7/1999
EP    0698209     2/1996

* cited by examiner

*Primary Examiner* — Gurpreet Kaur
(74) *Attorney, Agent, or Firm* — Welsh, Flaxman & Gitler LLC

(57) ABSTRACT

Method and apparatus for measurement of the oxygen partial pressure or the oxygen content in a measurement gas in at least one measurement cycle using a solid electrolyte cell having at least one oxygen-conducting solid electrolyte, and having at least one reference electrode as well as at least one measurement electrode, wherein the at least one measurement electrode is in communication with the measurement gas and the at least one reference electrode is in communication with a reference gas or reference volume separated from the measurement gas, wherein a current is imposed via the electrodes on the solid electrolyte cell for pump operation and a measurement voltage ($U_M$) is tapped at the electrodes.

14 Claims, 4 Drawing Sheets

METHOD AND APPARATUS FOR MEASUREMENT OF THE OXYGEN CONTENT OR THE OXYGEN PARTIAL PRESSURE IN A MEASUREMENT GAS

BACKGROUND OF THE INVENTION

1. Field of the Invention

The invention relates to a method for the measurement of the oxygen partial pressure or the oxygen content in a measurement gas in at least one measurement cycle using a solid electrolyte cell having at least one oxygen-conducting solid electrolyte, and having at least one reference electrode as well as at least one measurement electrode. The at least one measurement electrode is in communication with the measurement gas and the at least one reference electrode is in communication with a reference gas or a reference volume separated from the measurement gas. A current is imposed via the electrodes on the solid electrolyte cell for pump operation and a measurement voltage ($U_M$) is tapped at the electrodes.

2. Description of the Related Art

Methods and devices or sensors for measuring the oxygen content of a measurement gas are known in various designs. Oxygen sensors are known, for example, which operate according to a diffusion-limiting amperometric method. However, these oxygen sensors are only suitable to a certain extent for measurement at high air humidity, since as a result of the design of the sensor, moisture can penetrate into the interior of the respective oxygen sensor via diffusion openings and can lead to problems there. In particular, condensed moisture can lead to destruction of such a sensor upon starting up again.

Oxygen sensors are further known which operate according to a potentiometric method (Nernst cell). These sensors are predominantly used for measurement of small oxygen concentration in the area of exhaust gas monitoring. Due to the avoidance of diffusion openings, these sensors are more robust with respect to moisture. In order to determine the oxygen partial pressure or the oxygen content, the oxygen partial pressure of a reference gas or a reference volume is compared with the oxygen partial pressure of the measurement gas. More specifically, using a solid electrolyte cell in the simplest case includes at least one first electrode in the area of the reference gas, a second electrode in the area of the measurement gas and at least one oxygen-conducting solid electrolyte, for example, made of zirconium dioxide (zirconium IV oxide) between the first electrode and the second electrode. The measurement voltage applied to the electrodes determines, according to the so-called Nernst equation, the oxygen partial pressure quotient between the reference gas and the measurement gas. This simplified potentiometric method however assumes that the oxygen partial pressure in the reference volume is constant, i.e. the reference chamber accommodating the reference gas or reference volume is absolutely tightly sealed which in practice is not attainable or at best only with an economically unjustifiable expenditure.

In order to avoid this disadvantage, it is usual that the oxygen partial pressure in the reference volume is re-set at periodic intervals. Specifically, the reference volume is re-set using an additional solid electrolyte cell, which is located between the reference volume and the measurement gas, and the solid electrolyte cell is operated as a pure pump cell. However, this also means an additional, not inconsiderable, construction expenditure. The combination of the functions pumping and measuring in a single solid electrolyte cell has hitherto failed inter alia in that the voltage measured at the electrodes of such a solid electrolyte cell is additionally falsified by the voltage drop produced inside the solid electrolyte cell by the pump current, which is substantially dependent on the internal resistance of the solid electrolyte and is difficult to eliminate since the internal resistance of the solid electrolyte varies significantly with the temperature and lifetime thereof.

In particular, a method (EP 0 698 209) is also known in which an attempt is made to eliminate the disturbance variable produced by the voltage drop of the pump current whereby a solid electrolyte cell is alternately operated as pump and measurement cell. In this alternating mode, however polarisation effects occur which also falsify the measurement result.

In another known method (DE 198 00 027) it is proposed to reduce these polarisation effects which falsify the measurement result by a short current pulse having inverted polarity.

SUMMARY OF THE INVENTION

It is the object of the invention to provide a method which enables the oxygen partial pressure and, therefore, also the oxygen content in a measurement gas to be determined with high accuracy with a reduced expenditure on apparatus.

"Measurement gas" as used in the present disclosure is to be understood in the sense of the gas to be measured.

"Oxygen-conducting solid electrolyte" as used in the present disclosure is to be understood in the sense of the invention as an electrolyte which in a pump mode when acted upon by a pump current produces an oxygen transport depending on a quantity of charge carriers produced by the pump current and in measurement mode delivers a voltage corresponding to the quotient of oxygen partial pressure between a reference gas and a measurement gas.

The expression "substantially" or "approximately" as used in the present disclosure is to be understood in the sense of the invention to mean deviations from the exact value in each case of +/−10%, preferably of +/−5% and/or deviations in the form of insignificant changes for the function.

In a further development, the method according to the invention is executed, for example, so that the oxygen partial pressure in the first phase is reduced to a value significantly lower than 1% of the oxygen partial pressure of the measurement gas. The first phase is ended when the voltage applied to the electrodes in this phase exceeds a predetermined voltage threshold. The voltage threshold is composed of a variable component which is generated by a voltage drop of the pump current and a component which results from the oxygen partial pressure quotient. The voltage drop resulting from the pump current within the first phase is determined at a time at which the voltage applied to the electrodes is only or substantially only determined by the voltage drop of the pump current.

After the end of the first phase, the reference volume in a second phase is brought to a defined oxygen partial pressure by filling by the solid electrolyte cell operated in pump mode, which is of the order of magnitude of the oxygen partial pressure to be measured and that for this purpose a quantity of charge carriers is transported by means of the pump current, which is proportional to the oxygen partial pressure to be set in the reference volume. For setting a defined oxygen partial pressure in the reference volume during the second phase, the solid electrolyte cell is acted upon by at least one pump current pulse and the duration of the at least one pump current pulse is selected so that the current-time integral of the amplitude of the pump current pulse and the pulse duration corresponds to the quantity of charge carriers and is proportional to the oxygen partial pressure to be set in the reference volume. After the end of the second phase and preferably after the end of a third phase following the second phase and serving as a decay phase, the oxygen partial pressure of the measurement gas is determined from the measurement voltage applied in the measurement phase. The measurement cycle, comprising at least the first phase, the second phase and the measurement phase, is repeated periodically. The pump current (Ip) and/or the duration of the pump current (Ip) in the second phase are changed and/or set so that the measurement voltage measured in the measurement phase has a predefined constant or substantially constant voltage value. The oxygen partial pressure of the measurement gas is determined from the current-time integral of the amplitude of the pump current and the duration of the pump current in the second phase (phase II). The pump current (Ip) in the second phase is constant with regard to amplitude and profile. In order to achieve the predefined constant voltage value in the measurement phase, for example, zero voltage, the duration of the pump current in the second phase is set and/or regulated. The oxygen partial pressure of the measurement gas is determined from the duration of the pump current. The oxygen concentration is determined from the respective oxygen partial pressure at known ambient pressure, and/or the oxygen partial pressure of the reference volume is determined by means of a reference measurement with a known oxygen partial pressure of the measurement gas. For setting an internal resistance of the solid electrolyte cell which is a function of the temperature of the solid electrolyte cell or of the solid electrolyte or which is proportional to the temperature of the solid electrolyte cell or of the solid electrolyte, the sequence containing the first, second and third phase is repeated many times in a resistance setting method. Following the respective conditioning method, the internal resistance of the solid electrolyte cell is determined and with this resistance the cell temperature of the solid electrolyte cell is determined or the cell temperature of the solid electrolyte cell is controlled or regulated as a function of this resistance. The oxygen partial pressure in the reference volume is set as a function of the oxygen partial pressure in the measurement gas to be expected in the measurement, preferably in such a manner that the ratio "oxygen partial pressure in measurement gas/oxygen partial pressure in reference volume" is 2.7 or about 2.7, for example, 2.718, where the preceding process steps can each be used individually or in any combination.

Further developments, advantages and possible applications of the invention are also obtained from the following description of exemplary embodiments and from the figures. Here all the features described and/or depicted pictorially by them or in any combination are fundamentally the subject matter of the invention regardless of their summary in the claims and their back reference.

BRIEF DESCRIPTION OF THE DRAWINGS

The invention is explained in detail hereinafter with reference to the figures for exemplary embodiments. In the figures.

DETAILED DESCRIPTION OF THE INVENTION

Figure 1:
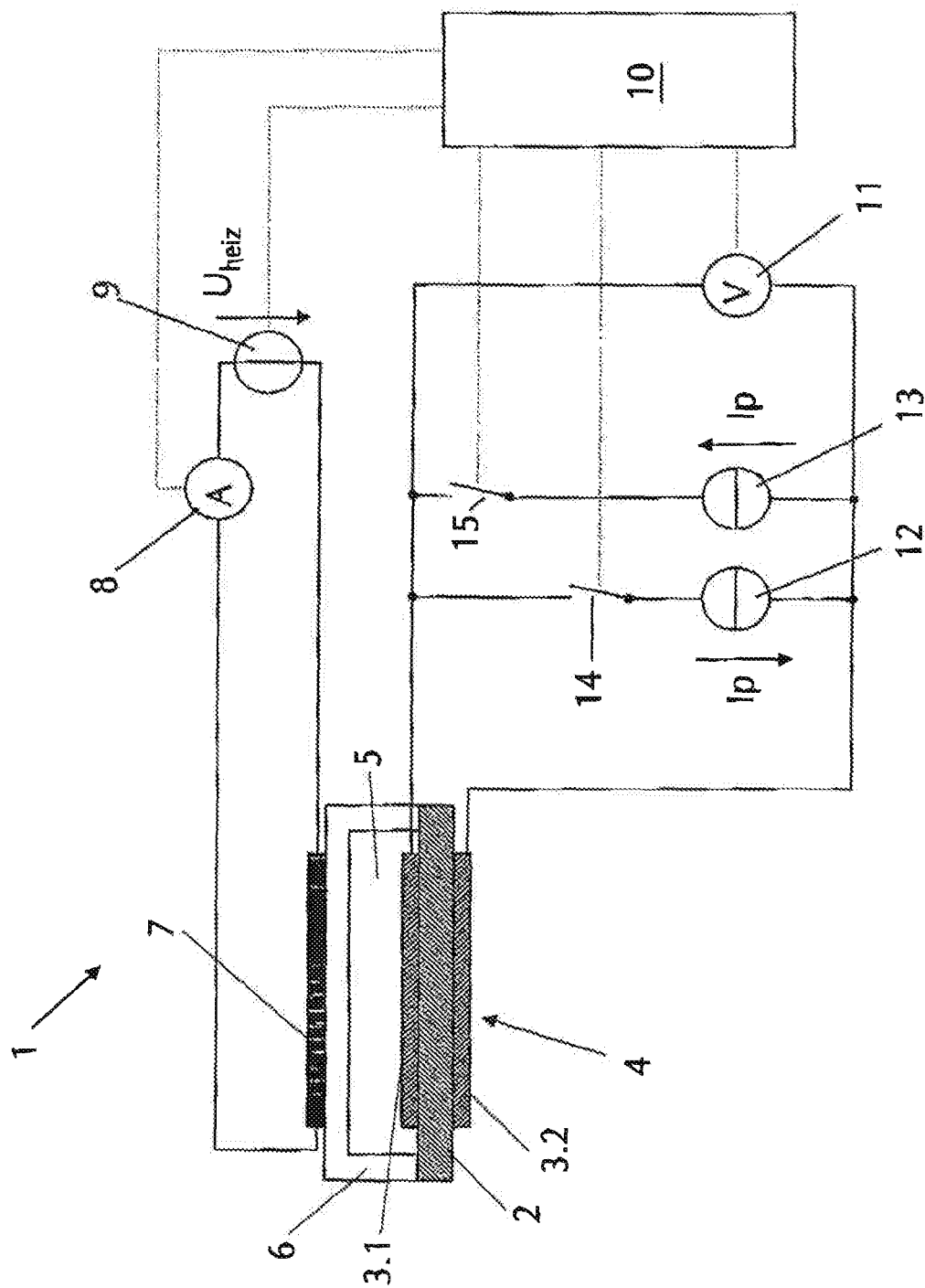
FIG. 1 shows in a simplified functional diagram an apparatus for determining the oxygen content of a measurement gas according to one embodiment of the invention.

The apparatus (sensor), designated in the figures generally as 1, is used for determining the oxygen partial pressure or the oxygen content of a measurement gas in a measurement gas volume or in a measurement gas environment. The apparatus 1 includes an oxygen-conducting solid electrolyte 2, e.g. made of zirconium dioxide. The substrate-like or plate-like solid electrolyte 2, in the embodiment shown, is provided on a first surface side with a reference electrode 3.1 and on its other opposite second surface side with a measurement electrode 3.2. Of these electrodes, which together form a solid electrolyte cell 4 together with the solid electrolyte 2, the reference electrode 3.1 is located in a reference chamber 5 which accommodates a reference volume, which is closed as tightly as possible by a cover 6. The measurement electrode 3.2 is located in the measurement gas environment carrying the measurement gas or in a room carrying the measurement gas. An electrical heater 7 is used for heating the solid electrolyte 2 to a constant or substantially constant operating temperature. This heater 7 is located sufficiently close to the solid electrolyte 2, i.e. in the embodiment shown, on the outer side of the cover 6, opposite the solid electrolyte 2. In order to keep the temperature constant, the heater 7 is located in a regulated heating current circuit which, inter alia, comprises a measuring device 8 for measuring the heating current and a voltage source 9 for generating the heating voltage $U_{Heiz}$. The heating current measured with the measuring device 8 is proportional to the temperature of the heater 7. The heating voltage $U_{Heiz}$ delivered by the voltage source 9 is controlled by a control, and monitoring unit 10 as a function of the heating current or the measurement signal of the measuring device 8 (as actual value) and a desired value stored in the control and monitoring unit 10. As a result, the desired constant or substantially constant temperature of the heater 7 and therefore operating or cell temperature for the solid electrolyte 2 or the solid electrolyte cell 4 is achieved.

The reference electrode 3.1 and the measurement electrode 3.2 are continuously connected to a high-resistance measuring device 11 (high-resistance voltmeter) for measurement of the measurement voltage $U_M$ applied between these two electrodes or between the two surface sides of the solid electrolyte 2. The measuring device 11 delivers a signal corresponding to the measured measurement voltage $U_M$ to the control and monitoring unit 10.

In FIG. 1, reference numerals 12 and 13 designate two current sources. The current source 12 is arranged in series with a controllable switch 14 between the reference electrode 3.1 and the measurement electrode 3.2. The current source 13 is arranged in series with a controllable switch 15 between the reference electrode 3.1 and the measurement electrode 3.2. The current source 12 is configured so that when the switch 14 is closed, it produces a current flow or pump current Ip through the solid electrolyte 2 from the measurement electrode 3.2 to the reference electrode 3.1. More specifically, the current source is configured for a pump mode of the solid electrolyte cell 4 for emptying the reference chamber 5, i.e. for reducing the oxygen partial pressure or the oxygen content in the reference chamber 5 or in the reference volume to a value which is significantly below the oxygen partial pressure or the oxygen content of the measurement gas and is, for example, less than 10% of the oxygen partial pressure or the oxygen content of the measurement gas or zero or substantially is zero (hereinafter for short "emptying of the reference chamber 5").

The current source 13 is configured so that when the switch 15 is closed it produces a current flow or pump current $I_P$ through the solid electrolyte 2 from the reference electrode 3.1 to the measurement electrode 3.3 and specifically for a pump mode of the solid electrolyte cell 4 for filling the reference chamber 5, i.e. for setting a reference oxygen partial pressure or content in the reference chamber 5 (hereinafter for short "filling of the reference chamber 5").

The rest position of the switches 14 and 15 is its open state. The switches 14 and 15 are also controlled by the control and monitoring unit 10 in the manner described in detail hereinafter and for this purpose, for example, are relays or electronic components, e.g. transistors.

As a result of the electrical internal resistance of the solid electrolyte cell 4 or the solid electrolyte 2 in the pump mode and as a result of polarization effects on changing between the pump mode and operation of the solid electrolyte cell 4 as a measurement cell (measuring mode), a potentiometric measuring mode, i.e. a determination of the oxygen concentration or the oxygen content in the measurement gas by measurement and evaluation of the measurement voltage $U_M$, is only possible with a suitable configuration of the measurement method.

Figure 2:
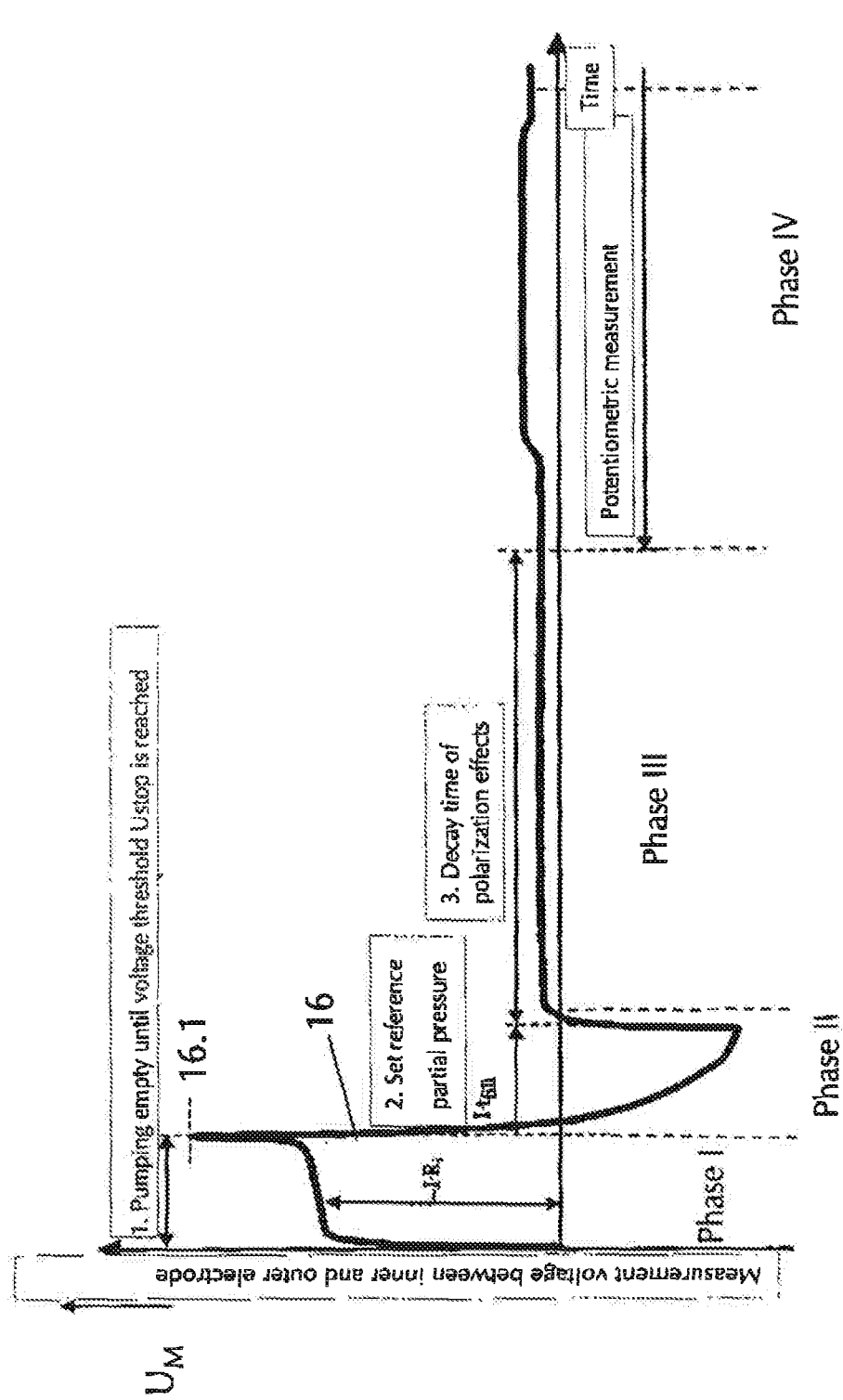
FIGS. 2 and 3 each show a voltage and time diagram of the measurement voltage in two different methods according to the invention.

Such a measurement method, or the time profile 16 of the measurement voltage $U_M$ in this method, is shown in FIG. 2. In order to be able to use the device 1 for potentiometric measurement of the absolute oxygen partial pressure or oxygen content in the measurement gas, it is necessary to bring the oxygen partial pressure or the oxygen content in the reference chamber 5 or in the reference volume there to a defined reference value. For this purpose, in a first step or in a first phase I of the measurement cycle, the solid electrolyte cell 4 with the switch 15 open is operated as a pump cell for emptying the reference chamber 5 by closing the switch 14. Here the profile of the measurement voltage $U_M$ is monitored. The measurement voltage $U_M$ is here substantially composed of an electromotive force caused by the oxygen partial pressure quotient of the oxygen partial pressures of the measurement gas and the reference gas, and of a voltage drop produced by the pump current Ip at the internal resistance of the solid electrolyte cell 4. This internal resistance is, inter alia, substantially dependent on the operating temperature of the solid electrolyte 2 and also on the age of the solid electrolyte 2. Small components of the voltage $U_M$ resulting from the electromotive force are in many cases barely measurable at the beginning of phase I and get lost in the voltage drop produced by the internal resistance of the solid electrolyte cell 4. However, the component of the voltage $U_M$ produced by the electromotive force, and therefore this voltage itself, increases significantly in the course of phase I when the oxygen partial pressure or oxygen content of the reference volume in the reference chamber 5 tends to zero and then significantly exceeds the influence of the voltage drop caused by the pump current Ip at the internal resistance of the solid electrolyte cell 4, as is indicated in FIG. 2 at 16.1. As a result, the end of the emptying of the reference chamber 5, or phase I, is clearly detectable, i.e. the time of the end of phase I can be defined clearly and simply by exceeding a predefined voltage threshold. In order to further reduce the influence of the pump current Ip, the corresponding voltage threshold can be defined relative to the typical voltage drop produced by the pump current Ip. This typical voltage drop caused by the pump current Ip can be determined, for example, during the phase I at the time at which the voltage component caused by the electromotive force still makes no significant contribution to the voltage $U_M$.

After completing the emptying of the reference chamber 5, in phase II the switch 14 is opened and the switch 15 is closed so that now the pump current Ip produced by the current source 13 flows in the opposite direction through the solid electrolyte cell 4 or the solid electrolyte 2 and oxygen is hereby pumped from outside into the reference chamber 5 for filling the reference chamber 5. The transported quantity of oxygen is proportional to the transported quantity of charge of the pump current through the solid electrolyte 2. By a pump current pulse having a defined current-time integral $Ixt_{fill}$ the oxygen partial pressure or oxygen content of the reference volume can be brought to a defined value. The relationship between the current-time integral of the pump current pulse and the oxygen partial pressure in the reference volume set with the pump current pulse is substantially obtained from the volume of the reference chamber 5 and can be determined by calibration.

After introducing the defined quantity of oxygen into the reference chamber 5, the switch 15 is also opened again. The solid electrolyte cell 4 is then operated as a pure measurement cell. After phase III and following the end of phase II, i.e. after decay of polarisation effects caused by the change between emptying and filling the reference chamber 5, in phase IV the oxygen partial pressure of the measurement gas at the electrode 3.2 is determined using the Nernst equation from the measurement voltage $U_M$ taking into account the set oxygen partial pressure in the reference chamber 5 known from the current-time integral of the pump current pulse during filling.

The previously described method with the four phases I-IV of the measurement cycle assumes that the reference chamber 5 is sufficiently tight so that the oxygen partial pressure in this reference chamber 5 remains constant over a fairly long time. In practice, however a periodic repetition of the measurement cycle with the phases I-IV will be required.

Figure 3:
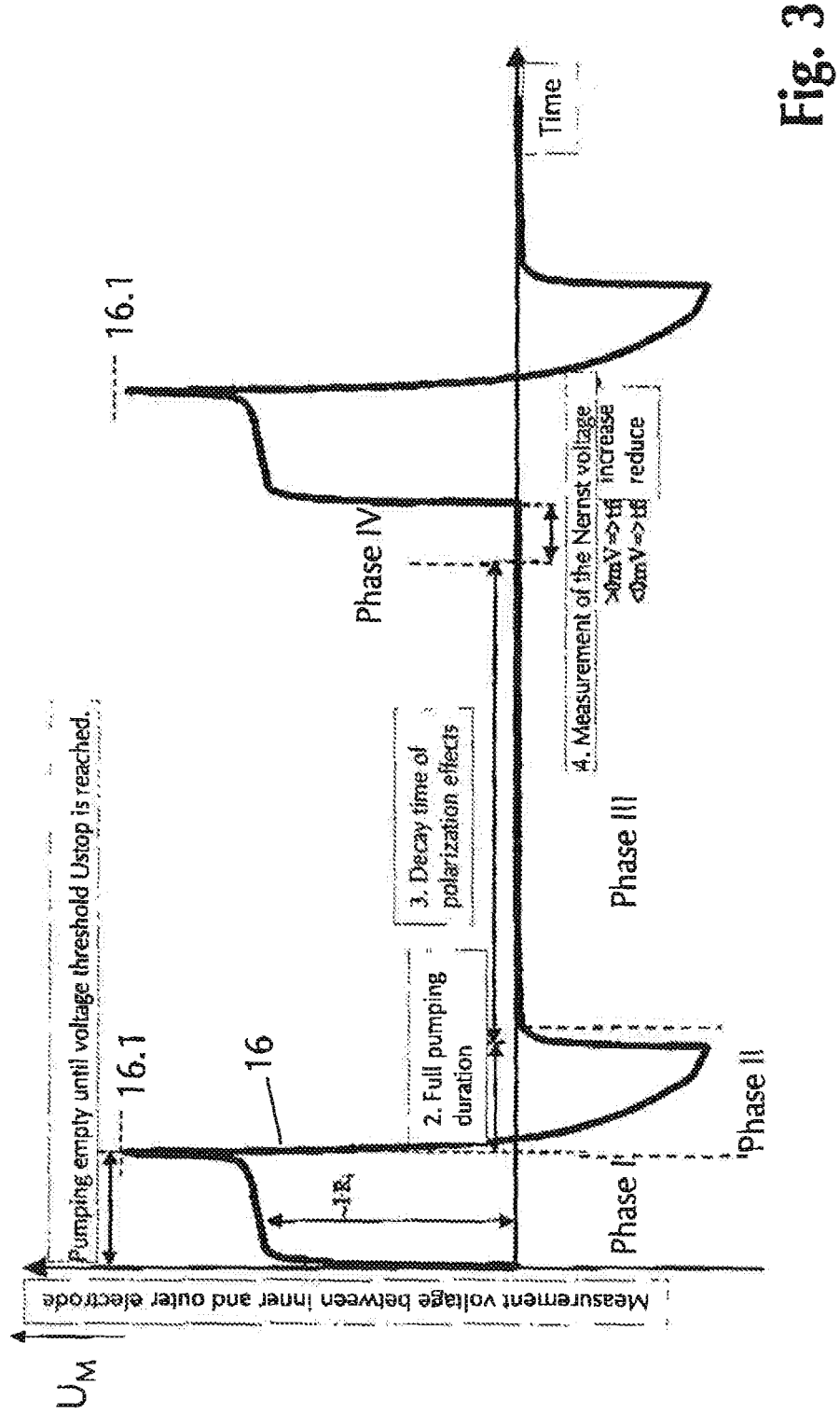

FIG. 3 shows the voltage-time profile 16 of the voltage $U_M$ in another method which can also be designated as a dynamic ampere-potentiometric measurement method. In this method a continuous repetition of phases I-IV takes place, i.e. a periodic emptying and filling of the reference chamber 5 via the solid electrolyte cell 4 (phases I and II) operated as a pump cell with a subsequent decay phase (phase III) and measurement phase (phase IV). In phase I when the switch 14 is closed the emptying of the reference chamber 5 takes place in the same way as was described for phase I in the method of FIG. 2. In phase II with the switch 15 closed, filling of the reference chamber 5 takes place by the pump current Ip of the current source 13. For this purpose the switch 15 is closed for a predefined time interval $t_{fill}$ and then opened again. This is then followed in phase III by the decay of the polarisation effects and in the subsequent phase IV by the measurement of the voltage $U_M$, i.e. the Nernst voltage which corresponds to the quotient of the oxygen partial pressure in the reference chamber 5 and the oxygen partial pressure in the measurement gas.

The particular feature of this dynamic ampere-potentiometric measurement method consists in that in the course of the method the time $t_{fill}$ or the closure time of the switch 15 is adjusted by the control and monitoring unit 10 as a function of the voltage $U_M$ measured in phase IV in such a manner that finally the voltage $U_M$ measured in this phase IV has a predefined value, for example, zero.

Figure 4:
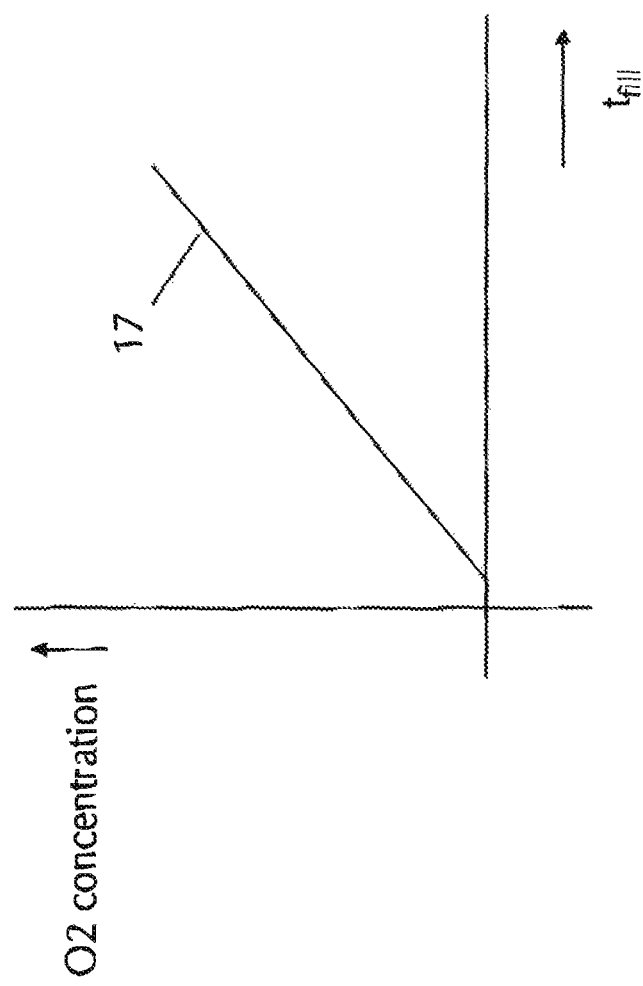
FIG. 4 shows in a diagram the dependence of the oxygen partial pressure or the oxygen content on the filling duration or time.

If the time $t_{fill}$, for example, is regulated so that the voltage $U_M$ in phase IV is zero, the oxygen partial pressure or oxygen content of the reference volume in the reference chamber 5 is equal to the oxygen partial pressure or the oxygen concentration of the measurement gas, i.e. at a predefined and constant pump current Ip during phase II the time $t_{fill}$ is directly proportional to the oxygen partial pressure or to the oxygen concentration in the measurement gas, as shown in FIG. 4 by curve 17. After a corresponding calibration, the time $t_{fill}$ can therefore be used directly as a measured value for the oxygen partial pressure in the measurement gas and when the pressure of the measurement gas is known, as a measured value for the oxygen content.

A variation of the internal resistance of the solid electrolyte cell 4 over the lifetime which adversely affects the method can be reduced by a method which can be designated as conditioning method or "burn-in" method. This method consists of a rapid sequence of phases I-III without dwelling in the potentiometric phase (IV). With such a reduced variation of the internal resistance, the internal resistance of the solid electrolyte cell 4 is then principally determined by its cell temperature and can be used as a control variable for this temperature. It is advantageous to regulate the heating of the solid electrolyte cell 4 so that the cell temperature remains constant. As a result, temperature dependences of the method can be reduced.

The temperature dependence of the method can also be reduced by another method:

By means of the Nernst equation a positive temperature coefficient is obtained for the resulting potentiometric cell or measurement voltage. With increasing cell temperature, however, an increase in the oxygen partial pressure in the reference volume is obtained by means of the general gas equation. However, this leads to a negative temperature coefficient. The ratio of oxygen partial pressure in the measurement gas to the oxygen partial pressure in the reference volume is crucial for whether the superposition of these two temperature influences leads to a positive or a negative overall temperature coefficient. If the typical oxygen partial pressures in the measurement gas are known in an application or measurement or the range in which the oxygen partial pressures in the measurement gas typically lie in an application or measurement, the influence of temperature can be reduced substantially by a favourable choice of oxygen partial pressure in the reference volume.

The temperature dependence is obtained on the one hand from the Nernst equation:

$$Un(T_{sens}, p_{O2Measgas}) = \frac{RT_{sens}}{zF} \ln\left(\frac{p_{O2Messgas}}{p_{O2Ref}}\right)$$

| | |
|---|---|
| Gas Constant | $R$ 8,314 J mol$^{-1}$ K$^{-1}$ |
| Faraday constant | $F = 96485$ C mol$^{-1}$ |
| Equivalent number | $z = 4$ |
| Sensor temperature | $T_{sens}$ in °K |
| Measurement gas | $p_{O2Messgas}$ in bar |
| Reference gas | $p_{O2Ref}$ in bar |

On the other hand, the reference partial pressure $p_{O2Ref}$ is temperature-dependent. For constant volume of the reference chamber, the following relationship is obtained:

$$p_{O2Ref}(T_{sens}) = p_{O2Ref0} \frac{T_{sens}}{T_{sens0}}$$

$p_{O2Ref0}$ is the reference partial pressure which was set at temperature $T_{sens0}$. Combining these gives:

$$Un(T_{sens}, p_{O2Messgas}) =$$
$$\frac{RT_{sens}}{4F}\ln\left(\frac{p_{O2Messgas}}{p_{O2Ref0}} \cdot \frac{T_{sens0}}{T_{sens}}\right) = \frac{RT_{sens}}{4F}\frac{T_{sens}}{T_{sens0}}\ln\left(\frac{p_{O2Messgas}}{p_{O2Ref0}} \cdot \frac{T_{sens0}}{T_{sens}}\right)$$

series expansion by $T_{sens}/T_{sens0} = 1$:

$$Un(T_{sens}, p_{O2Messgas}) =$$
$$\frac{RT_{sens0}}{4F}\left(\ln\left(\frac{p_{O2Messgas}}{p_{O2Ref0}}\right) + \underbrace{\left(\frac{T_{sens}}{T_{sens0}} - 1\right)\left(\ln\left(\frac{p_{O2Messgas}}{p_{O2Ref0}}\right) - 1\right)}_{=0 \text{ for reduction of the}} + \ldots\right) =$$

$$> \text{optimal ratio:} \frac{p_{O2Messgas}}{p_{O2Ref0}} = e \approx 2{,}718$$

It is therefore at least advantageous with an approximate knowledge of the oxygen partial pressures to be expected in the measurement gas, to select or set the oxygen partial pressure in the reference volume so that the preceding ratio "oxygen partial pressures in the measurement gas/oxygen partial pressure in the reference volume" of at least about 2.718 is obtained.

The invention has been described hereinbefore for exemplary embodiments. It is understood that numerous amendments or modifications are possible without thereby departing from the inventive idea forming the basis of the invention.

REFERENCE LIST

1 Apparatus for determining the oxygen content in a measurement gas
2 Solid electrolyte
3.1 Reference electrode
3.2 Measurement electrode
4 Cell
5 Reference chamber
6 Cover
7 Electrical heater
8 Current measuring device
9 Heating voltage source
10 Control and monitoring unit
11 Voltage meter
12, 13 Current source
14, 15 Switches
16 Time profile of the measurement voltage
16.1 Voltage maximum at the end of the emptying phase
17 Profile of oxygen partial pressure as a function of the filling time
$U_M$ Measurement voltage measured between the electrodes 3.1 and 3.2
$t_{fill}$ Filling time

What is claimed is:

1. A method for measurement of an oxygen partial pressure or an oxygen content in a measurement gas in at least one measurement cycle using a solid electrolyte cell having at least one oxygen-conducting solid electrolyte and having at least one reference electrode and at least one measurement electrode, wherein the at least one measurement electrode is in communication with the measurement gas and the at least one reference electrode is in communication with a reference gas or a reference volume separated from the measurement gas, the method comprising:

imposing a current via the at least one reference electrode and the at least one measurement electrode on the solid electrolyte cell for pump operation;

tapping a measurement voltage ($U_M$) at the at least one reference electrode and the at least one measurement electrode;

wherein in a first phase (phase I) of the at least one measurement cycle, an oxygen partial pressure of the reference volume is reduced via the solid electrolyte cell operated in a pump mode until the oxygen partial pressure is lower than an oxygen partial pressure of the measurement gas so that the measurement voltage ($U_M$) used in a measurement phase (phase IV) for determining an oxygen partial pressure or the oxygen content of the measurement gas is only or is substantially only determined by an oxygen partial pressure quotient between the oxygen partial pressure of the measurement gas and an oxygen partial pressure of the reference gas, wherein the oxygen partial pressure of the reference volume is determined by a reference measurement with a known oxygen partial pressure of the measurement gas.

2. The method according to claim 1, wherein an oxygen partial pressure in the first phase is reduced to a value significantly lower than 1% of the oxygen partial pressure of the measurement gas.

3. The method according to claim 1, wherein the first phase is ended when the measurement voltage ($U_M$) applied to the at least one reference electrode and the at least one measurement electrode in the first phase exceeds a predetermined voltage threshold.

4. The method according to claim 3, wherein the predetermined voltage threshold comprises a variable component which is generated by a voltage drop of a pump current (Ip) and a component which results from the oxygen partial pressure quotient and that the voltage drop resulting from the pump current (Ip) within the first phase (phase I) is determined at a time at which the measurement voltage ($U_M$) applied to the at least one reference electrode and at least one measurement electrode is substantially only determined by the voltage drop of the pump current.

5. The method according to claim 1, wherein after an end of the first phase, a reference volume in a second phase (phase II) is brought to a defined oxygen partial pressure by filling by the solid electrolyte cell operated in pump mode, which is of the order of magnitude of an oxygen partial pressure to be measured and a quantity of charge carriers is transported by a pump current, which is proportional to the oxygen partial pressure of the reference volume.

6. The method according to claim 5, wherein for setting a defined oxygen partial pressure in the reference volume during the second phase (phase II), the solid electrolyte cell is acted upon by at least one pump current pulse and the duration of the at least one pump current pulse is selected so that a current-time integral of an amplitude of the pump current pulse and the pulse duration corresponds to the quantity of charge carriers and is proportional to the oxygen partial pressure to be set in the reference volume.

7. The method according to claim 1, wherein after an end of the second phase and after an end of a third phase (phase III) following the second phase and serving as a decay phase, the oxygen partial pressure of the measurement gas is determined from the measurement voltage ($U_M$) applied in the measurement phase (phase IV).

8. The method according to claim 1, wherein the at least one measurement cycle, comprising at least the first phase (phase I), a second phase (phase II) and the measurement phase (phase IV), is repeated periodically.

9. The method according to claim 8, wherein a pump current (Ip) or a duration of the pump current (Ip) in the second phase (phase II) is changed or set so that the measurement voltage ($U_M$) measured in the measurement phase (phase IV) has a predefined substantially constant voltage value and that the oxygen partial pressure of the measurement gas is determined from a current-time integral of an amplitude of the pump current and a duration ($t_{fill}$) of the pump current (Ip) in the second phase (phase II).

10. The method according to claim 9, wherein the pump current (Ip) in the second phase (phase II) is constant with regard to amplitude and profile, and in order to achieve the predefined constant voltage value in the measurement phase (phase IV), the duration ($t_{fill}$) of the pump current (Ip) in the second phase (phase II) is set or regulated and that the oxygen partial pressure of the measurement gas is determined from the duration ($t_{fill}$) of the pump current (Ip) in the second phase (phase II).

11. The method according to claim 1, wherein an oxygen concentration is determined from a respective oxygen partial pressure at a known ambient pressure.

12. The method according to claim 1, wherein for setting an internal resistance of the solid electrolyte cell which is a function of a temperature of the solid electrolyte cell or of the solid electrolyte, a sequence containing the first phase, a second phase and a third phase is repeated many times in a resistance setting method.

13. The method according to claim 12, wherein following the resistance setting method and internal resistance of the solid electrolyte cell is determined and with the internal resistance, a cell temperature of the solid electrolyte cell is determined or the cell temperature of the solid electrolyte cell is controlled or regulated as a function of the internal resistance.

14. The method according to claim 1, wherein the oxygen partial pressure in a reference volume is set as a function of the oxygen partial pressure in the measurement gas to be expected during measurement in such a manner that a ratio of the oxygen partial pressure in the measurement gas to the oxygen partial pressure in the reference volume is approximately 2.7.

* * * * *